United States Patent
Rossi

(10) Patent No.: US 9,307,924 B2
(45) Date of Patent: Apr. 12, 2016

(54) METHOD AND RELATIVE DEVICE FOR SENSING AMPLITUDE AND PHASE OF AN ELECTRICAL SIGNAL

(75) Inventor: Stefano Rossi, Siena (IT)

(73) Assignee: STMICROELECTRONICS S.R.L., Agrate Brianza (MB) (IT)

( * ) Notice: Subject to any disclaimer, the term of this patent is extended or adjusted under 35 U.S.C. 154(b) by 1172 days.

(21) Appl. No.: 13/281,069

(22) Filed: Oct. 25, 2011

(65) Prior Publication Data

US 2012/0098520 A1 Apr. 26, 2012

(30) Foreign Application Priority Data

Oct. 26, 2010 (IT) .............................. VA2010A0078

(51) Int. Cl.
*A61B 5/04* (2006.01)
*A61B 5/0205* (2006.01)
*A61B 5/053* (2006.01)
*G01R 27/02* (2006.01)

(52) U.S. Cl.
CPC .............. *A61B 5/053* (2013.01); *A61B 5/04002* (2013.01); *A61B 5/0205* (2013.01); *G01R 27/02* (2013.01)

(58) Field of Classification Search
CPC ........ A61B 5/05; A61B 5/053; A61B 5/0535; A61B 5/0536; A61B 5/0537; A61B 5/0538
USPC ........................................................ 600/547
See application file for complete search history.

(56) References Cited

U.S. PATENT DOCUMENTS 6,970,738 B1 11/2005 Othman et al.

FOREIGN PATENT DOCUMENTS

EP 1754441 2/2007

OTHER PUBLICATIONS

Paterno et al., "Frequency-domain reconstruction of signals in electrical bioimpedance spectroscopy", Medical & Biological Engineering & Computing, vol. 47, No. 10, Oct. 2009, pp. 1093-1102.
Signorelli et al., VA2010A000078, "Low on-Resistance MOSFET Implemented DC Source Bypass or Circuit Breaker With Related Self-Supplied Controller Circuit Including Fire or Other Risk DC Output Disabling Means", May 2010, pp. 1-14.
Pallas-Areny, et al., "Bioelectric Impedance Measurements Using Synchronous Sampling", IEEE Transactions on Biomedical Engineering, vol. 40, No. 8, Aug. 1993, pp. 824-829.
Min, et al., "Synchronous Sampling and Demodulation in an Instrument for Multifrequency Bioimpedance Measurement", IEEE Transactions on Instrumentation and Measurement, vol. 56, No. 4, Aug. 2007, pp. 1365-1372.

*Primary Examiner* — Adam J Eiseman
(74) *Attorney, Agent, or Firm* — Allen, Dyer, Doppelt, Milbrath & Gilchrist, P.A.

(57) ABSTRACT

A method of sensing an amplitude and a phase of a varying electrical signal representing an impedance of an electrically conductive tissue through which an AC stimulation current is forced may include measuring a first amplitude value of the varying electrical signal corresponding to an arbitrary initial phase offset value and assuming the first amplitude value corresponds to the amplitude and assuming the arbitrary initial phase offset value corresponds to the phase. The method may include measuring a second amplitude value of the varying electrical signal at a phase offset different from the phase. The method may further include comparing the second amplitude value with the amplitude, and updating the amplitude and the phase to correspond to one of a maximum and a minimum amplitude value and to a corresponding phase offset.

16 Claims, 4 Drawing Sheets

METHOD AND RELATIVE DEVICE FOR SENSING AMPLITUDE AND PHASE OF AN ELECTRICAL SIGNAL

FIELD OF THE INVENTION

This invention relates to measurement instruments, and, more particularly, to a method and relative device for sensing amplitude and phase of an electrical signal.

BACKGROUND OF THE INVENTION

Techniques for measuring electrical impedance of the human body (bioimpedance) have been devised in bioengineering since the 1960s. These measurements include forcing an AC current through the body (usually at a frequency higher than 10 kHz, to avoid interference with the electrical activity of nervous and muscular tissues), and sensing the voltage drop between two points.

Water and all body fluids (blood, intra and extra cellular fluid, for example) provide the conductive medium of the body. Several measures and studies have been carried on, applying this technique in different parts or regions of the body and using different frequencies, to target different biological information. In numerous applications, only the absolute value of the bioimpedance is to be determined because it is simple to calculate and it provides useful information. In other applications, both amplitude and phase of the complex bioimpedance are measured.

It is relatively difficult to determine precise and reliable mathematical models of bioimpedance, particularly in thoracic regions. The main factors influencing electrical impedance in the chest are the blood in the heart and in the aorta, pleural fluids and pulmonary circulation. Heart pumping, that causes a variable distribution of blood in the heart-aorta region, and respiration are responsible of small variations of thoracic bioimpedance (i.e., the impedance of biologic tissues). From these variations it may be possible to determine heart rate, breath rate, and to evaluate cardiac output (volume of blood pumped by the heart over time).

There is a strong interest in methods of measuring the bioimpedance Zbody, because these measurements typically do not require an invasive technique and the bioimpedance may be correlated to a vast range of physiological parameters. Thus, information from bioimpedance measurements may be seen as potentially useful information in many medical fields.

Furthermore, the simplicity of the measurement, the integrability, reduced size, and low cost of the equipment, make the technique of measuring thoracic bioimpedance particularly suitable to be implemented in wearable or implantable health monitoring systems.

An AC voltage generated by an oscillator is used to control a voltage-to-current converter that delivers a current Iz that is injected through the biologic tissue using two or four electrodes. The voltage on the biologic tissue is sensed, amplified, and AM demodulated for obtaining a base-band signal. The voltage $V_Z(t)$ sensed on the electrodes is an AC signal modulated by the bioimpedance $Z(t)$:

$$V_Z(t)=|Z(t)|\cdot I_0 \cdot \cos(\omega t+\Phi(t))$$

With an AM demodulator it is possible to obtain a baseband signal representing the amplitude $|Z(t)|$ of the impedance, for example, by using the envelope demodulator depicted in FIG. 1, but the phase $\Phi(t)$ of $Z(t)$ would be still to be determined.

Another known technique, commonly referred to "synchronous sampling", for determining the amplitude $|Z(t)|$ and the phase $\Phi$ of the impedance, includes sampling the voltage $V_Z(t)$ twice in a period: a first sample p being synchronous with the carrier w, and the second sample q being delayed from the first one by one fourth of a carried period T, as schematically shown in FIG. 2. In the hypothesis that the amplitude $|Z(t)|$ is practically constant over each carrier period, the following equations hold:

$$p=|Z|\cdot I_0 \cdot \cos(\Phi)$$

$$q=-|Z|\cdot I_0 \cdot \sin(\Phi)$$

from which it is possible to calculate the amplitude and the phase of the impedance.

Unfortunately, these techniques require two sampling channels and relatively onerous calculations that cannot be executed by low cost devices.

An alternative to these onerous calculations includes approximating the amplitude of the bio-impedance with the average of the samples p and q taken into a same period, that is:

$$|Z| \cong \frac{p+q}{2\cdot I_0} = |Z|\cdot \frac{\cos(\Phi)-\sin(\Phi)}{2\cdot I_0} \quad (1)$$

This technique is suitable for low cost devices, because it may be implemented simply by low-pass filtering the sampled values, though the approximation becomes unacceptably coarse when the phase significantly differs from 0. Moreover, the phase of the bio-impedance is not calculated. A method to estimate the amplitude and the phase of the bio-impedance that may be implemented by low cost devices that have a low computational power may thus be desirable.

SUMMARY OF THE INVENTION

A method is directed to sensing amplitude and phase of a varying electrical signal representing the impedance of an electrically conductive tissue through which an AC stimulation current is forced. According to this method, a sample of the varying electrical signal is taken with a certain phase offset with respect to the AC stimulation current, and it is assumed that the sampled value is the real amplitude of the signal, and the phase is assumed equal to the phase offset. Another sample of the varying electrical signal is taken again either during the same period or in a different period, with a phase offset different from the assumed real phase. The corresponding sampled value is compared with the previously sampled amplitude, such to make the assumed real amplitude correspond to either the maximum or minimum sampled value and the assumed phase equal to the corresponding phase offset.

The varying electrical signal may be either the voltage on voltage sensing electrodes applied on a tissue when an AC stimulation current is forced through the same or through other electrodes applied on the tissue and through a portion of tissue comprised between the voltage sensing electrodes, or a low-pass filtered replica of the product between the voltage on the voltage sensing electrodes and an AC voltage outphased from the AC stimulation current by the phase offset. The method may be implemented with a sample and hold circuit controlled by a control unit.

DETAILED DESCRIPTION OF THE PREFERRED EMBODIMENTS

The present embodiments are disclosed referring to measurements of the impedance of a tissue carried out using four electrodes, because by using four electrodes the obtained measurements do not depend on the contact resistance between the sensing electrodes and the tissue, and thus are more refined. The embodiments may be usefully implemented also if measurements are carried out with only two electrodes. It will be considered that the varying electrical signal that is sampled is the voltage on the electrodes, though the same reasoning will apply also if the varying electrical signal is an amplified replica or even a noise-filtered replica of the voltage on the electrodes.

Figure 1A:
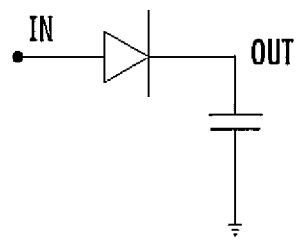
FIG. 1a is a schematic diagram of an AM demodulator according to the prior art.
Figure 1B:
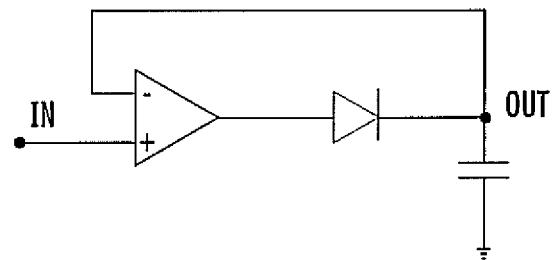
FIG. 1b is a schematic diagram of another AM demodulator according to the prior art.
Figure 3:
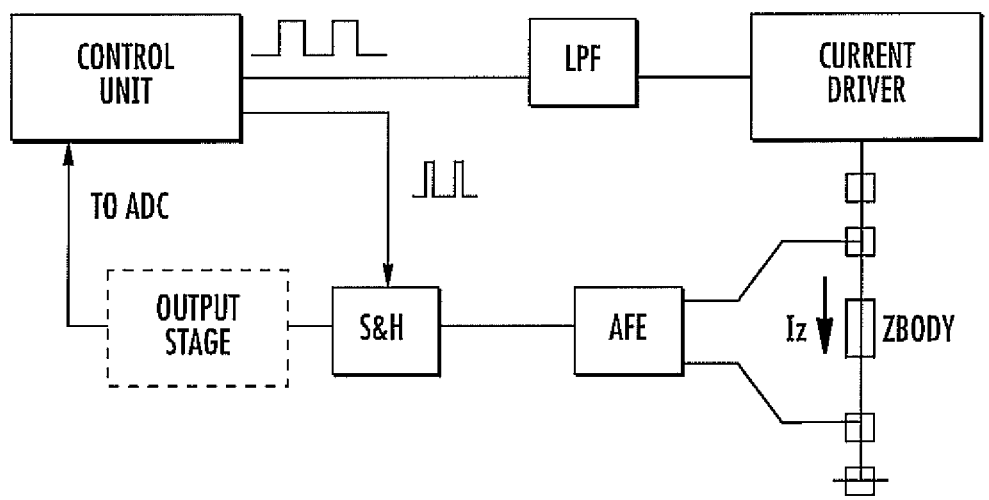
FIG. 3 is a schematic block diagram of a system for measuring the amplitude and the phase of bio-impedances according to the present invention.
Figure 2:
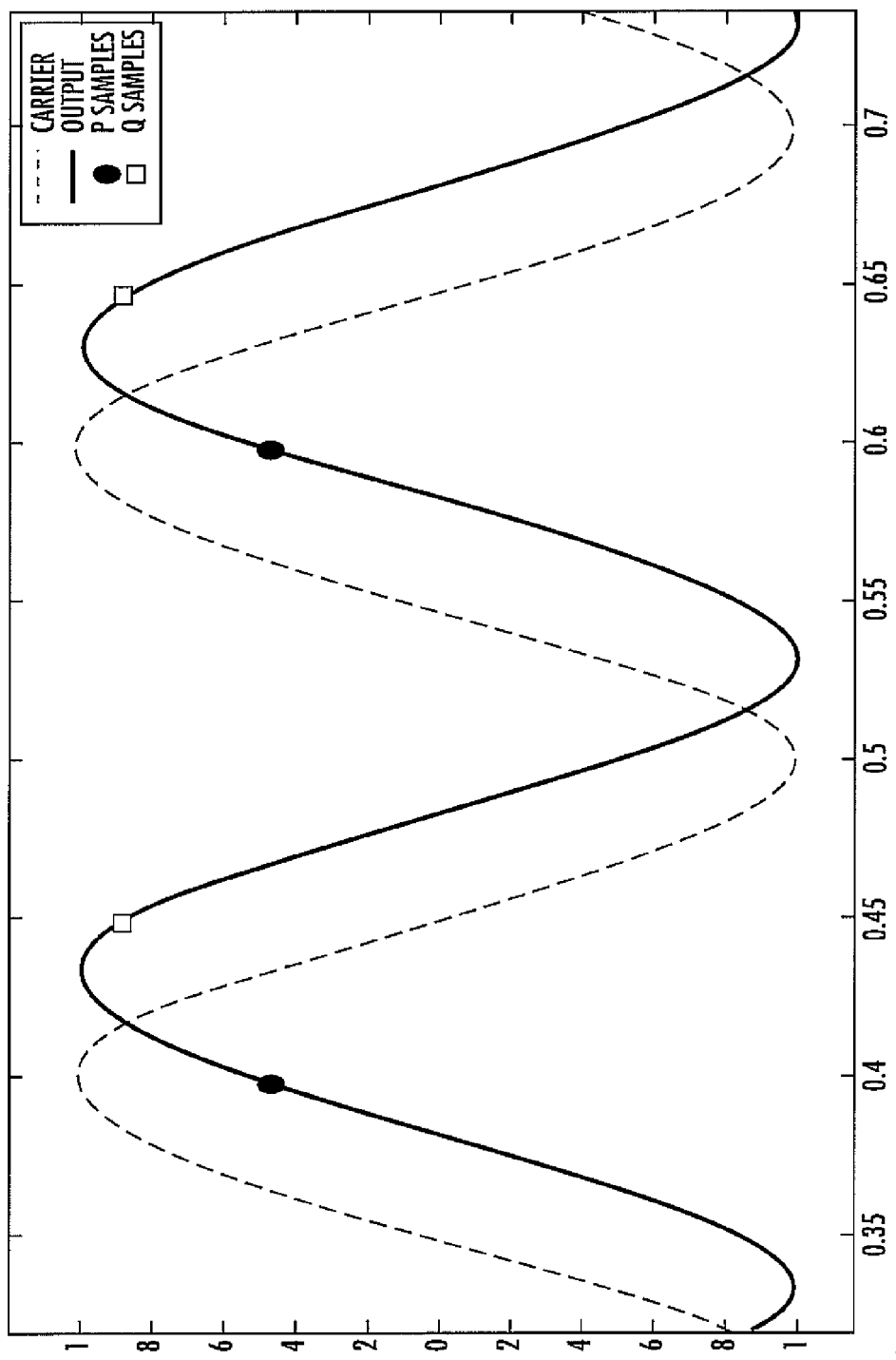
FIG. 2 is a time graph that illustrates the so-called "synchronous sampling" technique as in the prior art.

An embodiment of a system for measuring the amplitude and the phase of an electric signal is shown in FIG. 3. A current generator CURRENT DRIVER forces an AC stimulation current Iz throughout two electrodes and the portion of a living body comprised therebetween. The voltage drop on the electrodes is sensed by a sample and hold circuit S&H that samples this voltage drop at instants determined by a control unit CONTROL UNIT. This control unit generates logic pulses for enabling the sample and hold circuit, that on its turn, sends the sampled values to the control unit that processes it.

As an option, the sample and hold circuit may be coupled to the electrodes through an analog front end circuit AFE and/or may be coupled to the control unit through an output stage. The output stage may amplify the output of the sample and hold circuit and provide it to an analog-to-digital converter included in the control unit.

According to an embodiment, the current forced through the electrodes may be generated by a current driver controlled by a low-pass filtered replica of a clock signal at the frequency generated by the control unit itself. This technique of controlling the current generator is disclosed in Italian patent application No. VA2010R000043 in the name of the same applicant and herein incorporated by reference. As will be evident to any skilled person, the current generator may be controlled by another control unit distinct from the one depicted in the figure or in any appropriate way for letting it generate an AC current at any desired frequency.

The sample and hold circuit is controlled such to sample the electric signal corresponding to its peak value by the control unit DIGITAL UNIT that cooperates with the sample and hold circuit to implement the method. The frequency band of the bioimpedance signal is much lower than the frequency of the AC stimulation current, thus it may not be necessary to sample each peak of the electrical signal at each electrical period, but it is possible to downsample it if desired.

Figure 4:
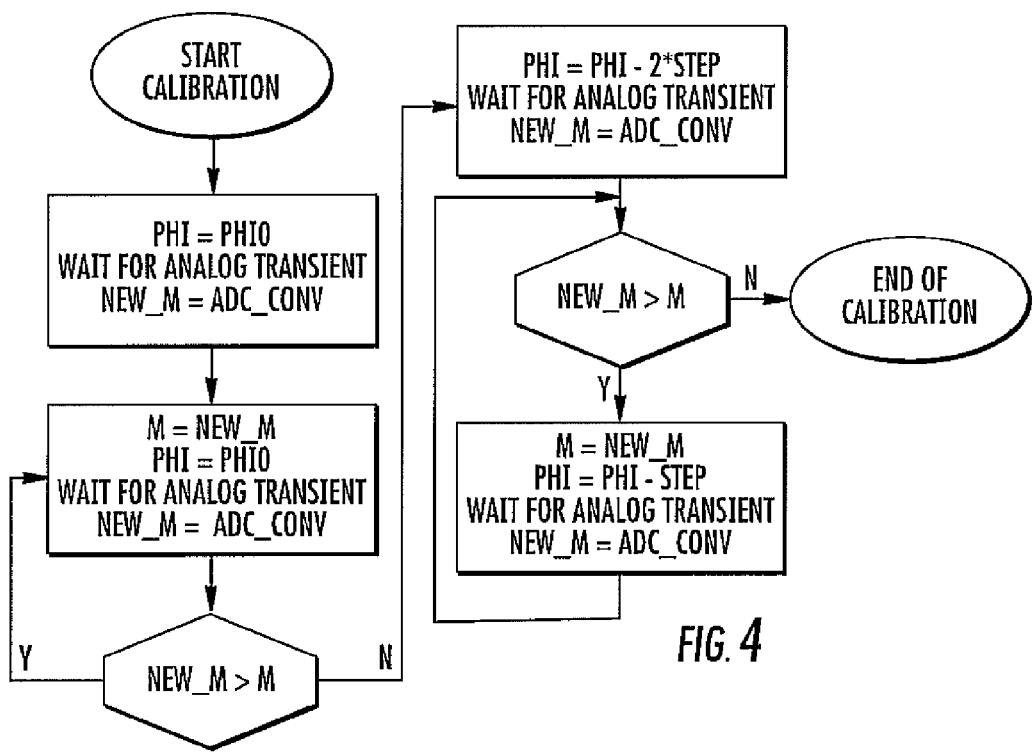
FIG. 4 is a flow chart of a method for measuring the amplitude and the phase of bio-impedances according to the present invention.

An embodiment of the method is schematically illustrated in FIG. 4. It is initially assumed that the real phase of the sensed voltage is equal to a certain value phi0, for example, a null value, and the amplitude of the voltage drop on the electrodes is sampled. This first sampled value is stored as the assumed real amplitude of the bio-impedance. Then the assumed phase is either increased or decreased by a certain step, the amplitude of the sensed voltage is sampled corresponding to the new phase value and is compared with the stored value of the assumed real amplitude: if the latter is smaller than the former, the assumed real amplitude and assumed real phase are updated, otherwise the previously stored values are kept unchanged.

If the phase value has been increased (respectively, decreased) and the assumed real amplitude and phase have been updated, at the next method step the assumed phase is yet increased (respectively, decreased), otherwise it will be decreased (respectively increased). The amplitude is sampled and compared with the previous value. If the value is greater than the previously sampled value, then the values of the assumed amplitude and of the assumed phase are updated, otherwise the procedure is stopped. In this way the positive peak of the sensed voltage is identified. Alternatively, the negative peak can be identified by updating the values of assumed real amplitude and phase if the new acquired value is smaller (instead of greater) than the previous one.

According to yet another embodiment, the varying electrical signal is a low-pass filtered replica of the product of the voltage sensed on the electrodes by an AC voltage outphased with respect to the AC stimulation current by the phase offset. Being $$V_Z(t)=|Z(t)|\cdot I_0\cdot\cos(\omega t+\Phi(t))$$

the voltage drop on the electrodes, and $$V_{AC}(t)=V_{AC}\cdot\cos(\omega t+\phi)$$

the AC voltage outphased with respect to the AC stimulation current by the phase offset $\phi$, then a low-pass filtered replica of the product of $V_Z$ by $V_{AC}$ is $$\frac{|Z(t)|\cdot I_0\cdot V_{AC}}{2}\cdot\cos(\Phi(t)-\phi)$$

By varying the phase $\phi$ according to the procedure described above, it is possible to find the assumed real phase:

$$\phi=\Phi$$

And the assumed real amplitude is:

$$\frac{|Z(t)|\cdot I_0\cdot V_{AC}}{2}$$

that is proportional to the amplitude $|Z|$ of the bioimpedance.

For both the embodiments, the varying phase $\phi$ is updated with discrete steps. Thus the final assumed phase $\phi$ differs from the real phase $\Phi$. The smaller the calibration steps are, the smaller the error on the phase. The error on the amplitude due to the approximation in the estimation of the phase is $$1-\cos(\Phi(t)-\phi)$$

that results small if the varying phase φ is adjusted with a small calibration step.

Figure 5:
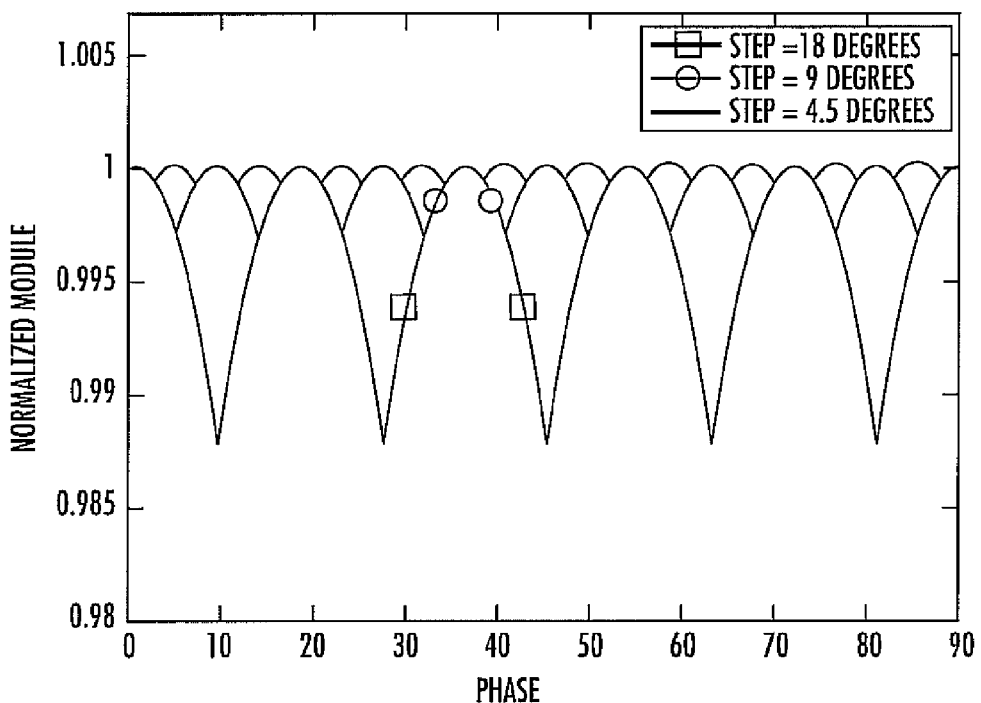
FIG. 5 is a graph comparing errors made in calculating the amplitude of the bio-impedance with respect to the impedance phase for different values of the approximation step of the method of the present invention.

FIG. 5 shows the measured values of the amplitude of the bio-impedance, normalized to the real amplitude of the bio-impedance, for different increment steps. Even with a phase resolution of 18 degrees, that is relatively coarse, the maximum approximation error is smaller than 2%.

Figure 6:
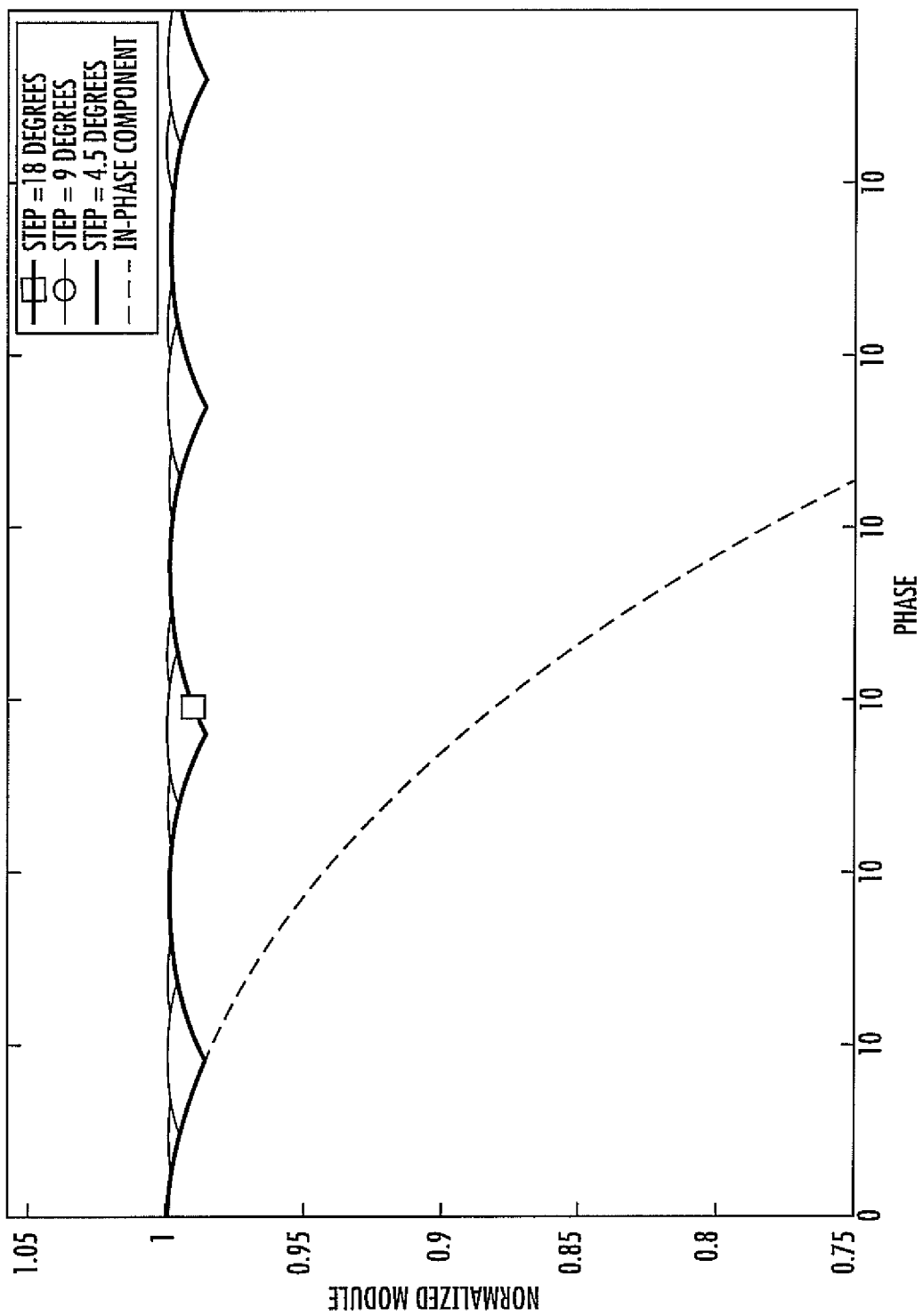
FIG. 6 is a graph that compares the errors made in calculating the amplitude of the bio-impedance with respect to the impedance phase for different values of the approximation step of the method of the present invention and using equation (1).

FIG. 6 compares the amplitude estimation errors according to the present method vs. the error (dashed line) in estimating the amplitude using equation (1). The errors made with the method described herein are bounded by a relatively narrow range for any value of the phase of the bio-impedance. By contrast, the approximation error using equation (1) becomes unacceptably great even for small phases of the bio-impedance.

That which is claimed:

1. A method of sensing an impedance of an electrically conductive tissue through which an AC stimulation current is forced, comprising:
    taking a first sample of a varying electrical signal representing the impedance based upon an arbitrary initial phase offset with respect to a null phase of the AC stimulation current and assuming the first sampled value as a real amplitude of a modulating signal and the arbitrary initial phase offset as a real phase;
    taking at least one second sample of the varying electrical signal at a phase offset different from the assumed real phase; and
    comparing the at least one second sample with the assumed real amplitude, and updating at each period the assumed real amplitude and assumed real phase such as to correspond either to a maximum or minimum sample corresponding phase offset; and
    when the AC stimulation current is forced through a portion of tissue between voltage sensing electrodes, generating the varying electrical signal by
        changing a phase of an AC voltage with respect to the AC stimulation current by the phase offset,
        calculating a product between the AC voltage and a voltage of the voltage sensing electrodes applied on a tissue,
        generating a replica of the product, and
        low-pass filtering the replica.

2. The method of claim 1, wherein at every successive sampling the phase offset different from the assumed real phase is chosen by at least:
    setting a phase offset either smaller or greater than the assumed real phase and sampling an amplitude of the varying electrical signal;
    comparing the newly sampled amplitude with the assumed real amplitude;
    determining either a maximum value or a minimum value of the varying electrical signal by repeating the setting and comparing steps with different phase offsets; and
    updating the assumed real amplitude and the assumed real phase to be equal to either a maximum or a minimum sample, and to the corresponding phase offset, respectively.

3. The method of claim 1, wherein if the sampled amplitude is greater than the assumed real amplitude, updating the assumed real amplitude to the newly sampled amplitude and the assumed real phase to set a phase offset for the new sampling, otherwise setting a phase offset either greater or smaller, respectively, and repeating the updating or setting steps.

4. The method of claim 1, wherein the arbitrary initial phase offset value is set to a value chosen in a range from 0 to 30 degrees.

5. A method of sensing an impedance of an electrically conductive tissue through which an AC stimulation current is forced, comprising:
    taking a first sample of a varying electrical signal representing the impedance based upon an arbitrary initial phase offset and assuming the first sampled value as a real amplitude of a modulating signal and the arbitrary initial phase offset as a real phase;
    taking at least one second sample of the varying electrical signal at a phase offset different from the assumed real phase; and
    comparing the at least one second sample with the assumed real amplitude, and updating at each period the assumed real amplitude and assumed real phase such as to correspond either to a maximum or minimum sample corresponding phase offset; and
    when the AC stimulation current is forced through a portion of tissue between voltage sensing electrodes, generating the varying electrical signal by
        changing a phase of an AC voltage with respect to the AC stimulation current by the phase offset,
        calculating a product between the AC voltage and a voltage of the voltage sensing electrodes applied on a tissue,
        generating a replica of the product, and
        low-pass filtering the replica.

6. The method of claim 5, wherein the first sample is based upon an arbitrary initial phase offset with respect to a null phase of the AC stimulation current.

7. The method of claim 5, wherein the assumed real amplitude and assumed real phase are updated at each period.

8. The method of claim 5, wherein at every successive sampling the phase offset different from the assumed real phase is chosen by at least:
    setting a phase offset either smaller or greater than the assumed real phase and sampling an amplitude of the varying electrical signal;
    comparing the newly sampled amplitude with the assumed real amplitude;
    determining either a maximum value or a minimum value of the varying electrical signal by repeating the setting and comparing steps with different phase offsets; and
    updating the assumed real amplitude and the assumed real phase to be equal to either a maximum or a minimum sample, and to the corresponding phase offset, respectively.

9. The method of claim 8, wherein if the sampled amplitude is greater than the assumed real amplitude, updating the assumed real amplitude to the newly sampled amplitude and the assumed real phase to set a phase offset for the new sampling, otherwise setting a phase offset either greater or smaller, respectively, and repeating the updating or setting steps.

10. The method of claim 5, wherein the arbitrary initial phase offset value is set to a value chosen in a range from 0 to 30 degrees.

11. A device for sensing an impedance of an electrically conductive tissue through which an AC stimulation current is forced providing a modulated electrical signal, the device comprising:
    a sample and hold circuit configured to be controlled by a logic control signal, receive a varying electrical signal representing an impedance for sampling the varying electrical signal when the logic control signal is asserted, and output sampled amplitude values;
a control unit configured to read the sampled amplitude values and generate logic control signals for
taking a first sample of the varying electrical signal representing the impedance based upon an arbitrary initial phase offset with respect to a null phase of the AC stimulation current and assuming the first sampled value as a real amplitude of a modulating signal and the arbitrary initial phase offset as a real phase,
taking at least one second sample of the varying electrical signal at a phase offset different from the assumed real phase, and
comparing the at least one second sample with the assumed real amplitude, and updating at each period the assumed real amplitude and assumed real phase such as to correspond either to a maximum or minimum sample corresponding phase offset; and
an AC current generator configured to
supply AC current to electrodes applied to the tissue for forcing the AC stimulation current therethrough, and
when the AC stimulation current is forced through a portion of tissue between the electrodes, generating the varying electrical signal by changing the phase of an AC voltage with respect to the AC stimulation current by the phase offset,
calculating a product between the AC voltage and a voltage of the voltage sensing electrodes applied on a tissue, and
generating a replica of the product, and
low-pass filtering the replica.

12. The device of claim 11, further comprising
an analog front end stage configured to sense a voltage drop on at least a portion of the tissue between the electrodes and generate the varying electrical signal at an input of said sample and hold circuit.

13. The device of claim 11, further comprising an analog stage coupled between said sample and hold circuit and said control unit.

14. A device for sensing an impedance of an electrically conductive tissue through which an AC stimulation current is forced providing a modulated electrical signal, the device comprising:

a sample and hold circuit configured to sample a varying electrical signal representing an impedance, and output sampled amplitude values;
a control unit configured to read the sampled amplitude values and generate logic control signals for
taking a first sample of the varying electrical signal representing the impedance based upon an arbitrary initial phase offset with respect to a null phase of the AC stimulation current and assuming the first sampled value as a real amplitude of a modulating signal and the arbitrary initial phase offset as a real phase,
taking at least one second sample of the varying electrical signal at a phase offset different from the assumed real phase, and
comparing the at least one second sample with the assumed real amplitude, and updating at each period the assumed real amplitude and assumed real phase such as to correspond either to a maximum or minimum sample corresponding phase offset; and
an AC current generator configured to
supply AC current to electrodes applied to the tissue for forcing the AC stimulation current therethrough, and
when the AC stimulation current is forced through a portion of tissue between the electrodes, generating the varying electrical signal by changing the phase of an AC voltage with respect to the AC stimulation current by the phase offset,
calculating a product between the AC voltage and a voltage of the voltage sensing electrodes applied on a tissue, and
generating a replica of the product, and
low-pass filtering the replica.

15. The device of claim 14, further comprising
an analog front end stage configured to sense a voltage drop on at least a portion of the tissue between the electrodes and generate the varying electrical signal at an input of said sample and hold circuit.

16. The device of claim 14, further comprising an analog stage coupled between said sample and hold circuit and said control unit.

* * * * *

UNITED STATES PATENT AND TRADEMARK OFFICE
CERTIFICATE OF CORRECTION

| | | |
|---|---|---|
| PATENT NO. | : 9,307,924 B2 | Page 1 of 1 |
| APPLICATION NO. | : 13/281069 | |
| DATED | : April 12, 2016 | |
| INVENTOR(S) | : Stefano Rossi | |

It is certified that error appears in the above-identified patent and that said Letters Patent is hereby corrected as shown below:

Title page, item (73)  Delete: "STMICOELECTRONICS S.R.L."
Insert --STMICROELECTRONICS S.R.L.--

Signed and Sealed this
Seventh Day of June, 2016

Michelle K. Lee
*Director of the United States Patent and Trademark Office*